United States Patent [19]

Reichley

[11] 4,215,984
[45] Aug. 5, 1980

[54] DENTAL SUCTION DEVICE

[76] Inventor: Joseph P. Reichley, 20 Davis Ave., Enon, Ohio 45323

[21] Appl. No.: 3,230

[22] Filed: Jan. 15, 1979

[51] Int. Cl.² .................................................. A61C 17/04
[52] U.S. Cl. ............................................................ 433/93
[58] Field of Search .................. 128/15; 32/33; 433/93

[56] References Cited

U.S. PATENT DOCUMENTS

| | | | |
|---|---|---|---|
| 2,436,040 | 2/1948 | Friedman | 32/33 |
| 2,701,916 | 2/1955 | Jarboe | 32/33 |
| 3,090,122 | 5/1963 | Erickson | 32/33 |
| 3,101,544 | 8/1963 | Baugham | 32/33 |
| 3,101,545 | 8/1963 | Baugham | 32/33 |
| 3,396,468 | 8/1968 | Dayhoff | 32/33 |
| 3,456,348 | 7/1969 | Lanigan | 32/33 |
| 3,631,598 | 1/1972 | Lussier | 32/33 |
| 4,053,984 | 10/1977 | Moss | 32/33 |

Primary Examiner—Robert Peshock
Attorney, Agent, or Firm—Biebel, French & Nauman

[57] ABSTRACT

A dental suction device is provided in which the generally hollow U-shaped base of the device is designed to be positioned in a patient's lower jaw area inside the lower row of teeth. The base is connected to a hollow, curved stem which can be connected to a suction source. Slots in the base are utilized to ingest excess moisture present in a patient's mouth during dental procedures. The device also has a flat plate attached to the base which acts as a tongue depressor and an adjustable tooth rest on the stem on which a patient's upper maxillary incisal teeth rest during dental procedures.

7 Claims, 5 Drawing Figures

DENTAL SUCTION DEVICE

BACKGROUND OF THE INVENTION

This invention relates to dental appliances, and more particularly to an improved device for collecting and removing debris and saliva from the mouth of a patient while maintaining a clear operating field during the conduct of dental procedures therein.

During dental operations such as drilling, filling, and taking impressions for crown and bridge work, it is desirable and in some cases absolutely necessary that the work area in the mouth be maintained as free of liquid as possible. The use of high speed drills requiring the use of a liquid coolant continuously provided to the point of drill contact makes the use of a suction device to continuously withdraw such fluid, as well as saliva and other debris, from the mouth of a patient, a necessity.

When lower crown and bridge impressions are being taken, problems unique to that particular dental procedure require that the impression site be devoid of any excess moisture. This is because the plastic or rubber material used to make such impressions will not form an accurate impression if excess moisture is present. Thus, such a dental procedure requires a suction device that will continuously and efficiently remove all excess moisture, such as rinse water, saliva, or blood, from the entire area around the site where the impression is to be taken, However, the device must be small enough to be able to fit comfortably into the mouth around the inside of the lower teeth of the patient while still permitting access of the tray which carries the impression material. Additionally, the device must be able to control the tongue to keep it away from the impression site.

Prior suction devices have utilized multiple orifice structures to expel moisture from the mouth of a patient as disclosed by Friedman, U.S. Pat. No. 2,436,040; Baughan, U.S. Pat. No. 3,101,545; and Lussier, U.S. Pat. No. 3,631,598. Still, other prior dental suction devices have utilized, at least in part, generally U-shaped tubes to evacuate the lower jaw area of patients during dental operations. Examples of such devices are shown by Van Lanigan, U.S. Pat. No. 3,456,348; Dayholl, U.S. Pat. No. 3,396,468; and Jarboe, U.S. Pat. No. 2,701,916. Finally, Erickson, U.S. Pat. No. 3,090,122 discloses a dental suction device which incorporates a bite block permitting a patient to grip the suction device in his or her teeth during dental operations.

However, none of the above-mentioned prior dental suction devices address or solve the unique problems associated with making accurate lower crown and bridge work impressions. Accordingly, the need still exists in the art for a dental suction device which will continuously and efficiently remove excess moisture from a patient's mouth and control the movement of a patient's tongue, and yet be sized such that there is access permitted for the tray containing the impression material.

SUMMARY OF THE INVENTION

In accordance with the present invention there is provided a dental suction device for use during dental procedures, such as lower crown and bridge impression work, cementing bands and direct-bonding orthodontia procedures, and any dental work done without the aid of an assistant. The dental suction device of the present invention has a generally U-shaped metal tubular base with liquid evacuation slots and holes therein, attached to a curved, generally upright metal tubular member and tubular stem, the end of which can be connected to a standard suction hose. The U-shaped portion of the device is sized to fit into the mouth of a patient in the lower jaw area inside of the lower teeth. It is provided with a plurality of liquid evacuation slots and holes extending through the lower half of the metal tubular base and spaced along the length of the device, through which it is possible to evacuate any excess liquid, saliva, or solid debris from the impression area.

The curved, upstanding tubular member has attached to the lower end thereof an elliptically shaped metal plate which is bent to follow the general curvature of the upstanding tubular member and act as a tongue depressor. In its preferred form, the plate has an elliptically shaped aperture in its central portion through which the upstanding tubular member extends.

At the opposite end of the upstanding tubular member there is provided a tubular stem having an adjustable collar on which a tooth rest is attached. A set screw on the collar can be loosened to correctly position the tooth rest for each individual patient. When the suction device is properly positioned in the mouth of the patient, the position of the tooth rest is adjusted so that when the patient's mouth is opened, the upper maxillary incisal teeth will fit over the rest. In this manner, the patient's mouth will be opened far enough to permit the dentist to work freely at properly positioning and seating the impression tray.

The suction device may also be designed so that the tubular stem is detachable from the rest of the device so that it can be removed after the impression tray has been seated while leaving the remainder of the suction device in the patient's mouth.

A rubber bite ball and extension may also optionally be attached to the collar on the tubular stem of the tooth rest so that certain types of bites may be stabilized. The collar on the stem is rotated 180° as that the bite ball and extension frictionally engage a patient's front teeth or gums when slippage off the tooth rest might occur.

As can be appreciated, it is an object of this invention to provide a suction device which will remove all excess moisture from a patient's mouth during dental procedures including the making of lower crown and bridge impressions; it is another object of this invention to provide a suction device which, when in place in a patient's mouth, will depress the patient's tongue and maintain it away from the field of operation; it is another object of this invention to provide a suction device having an adjustable tooth rest to maintain a patient's mouth in the open position during dental procedures. These and other objects of the invention will become apparent from the following description, the accompanying drawings, and the appended claims.

DESCRIPTION OF THE PREFERRED EMBODIMENTS

Figure 1:
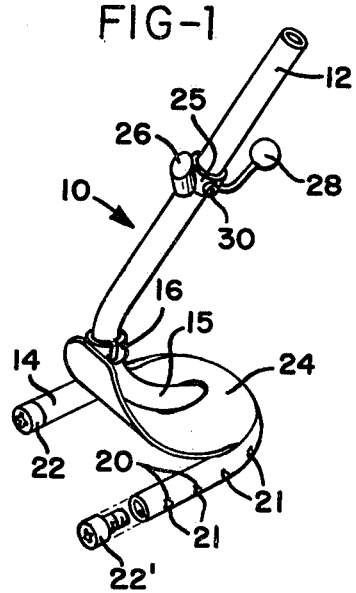
FIG. 1 is a perspective view of the suction device of this invention.
Figure 2:
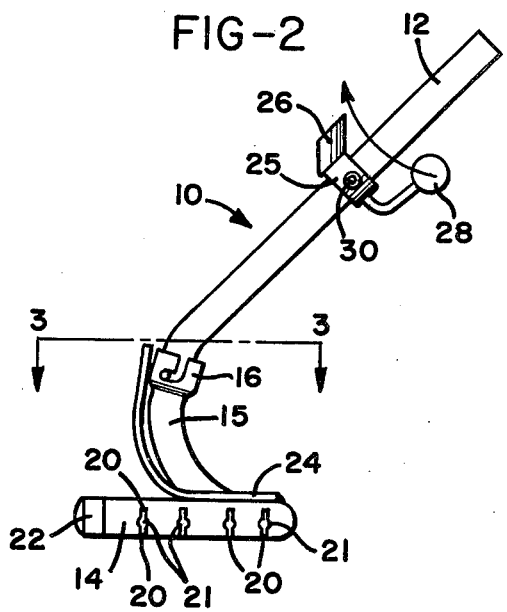
FIG. 2 is a side elevational of the device.
Figure 3:
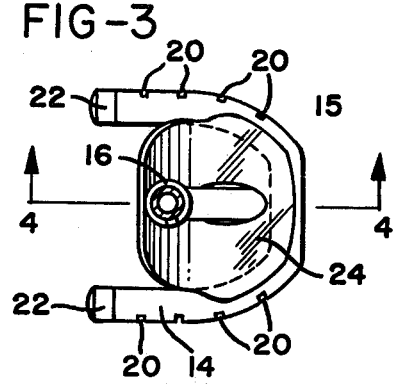
FIG. 3 is a top view of the device.
Figure 4:
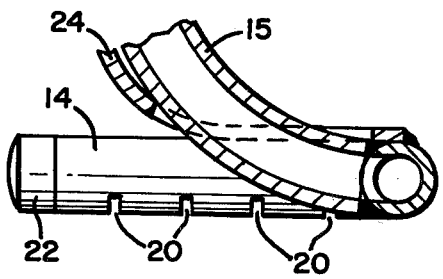
FIG. 4 is a sectioned view of the base of the device taken along line 4—4 in FIG. 3.

As shown in FIGS. 1-4, dental suction device 10 has a hollow tubular stem 12, a generally U-shaped tubular base 14, and a short, curved, tubular member 15 in fluid connection therewith. Tubular member 15 extends upwardly to join stem 12 at collar 16. As best illustrated in FIG. 2, collar 16 has an L-shaped slot into which an extension knob on tubular stem 12 slidingly fits. It is locked into place by rotating stem 12.

Preferably, the entire suction device is fabricated of a metal such as stainless steel. Alternatively, it may be made from a sturdy plastic material such as polystryrene or the like. The suction devices may be made in several sizes to fit both adult and younger patient's mouths.

Tubular base 14 has a plurality of slots 20 extending transversely through the lower half of the base and spaced along the length of the U-shaped member. Optionally, holes 21 may be provided as further openings in the tubular base 14. When a suction hose 32 (shown in FIG. 5) connected to a vacuum source is attached to the tip of stem 12, a sucking force is exerted through hollow stem 12, tubular member 15 and tubular base 14, and slots 20 and holes 21 to evacuate any excess liquid present in the mouth of a patient. Clean-out screws 22 and 22' are threadingly engaged on the end of tubular base 14 and can be removed periodically to clean out any debris which may accumulate in the member.

A flat elliptically shaped plate 24 is attached to member 15 and generally follows its curvature. In the embodiment illustrated in FIGS. 1-4, plate 24 has an elliptically shaped aperture located in its center through which member 15 passes. The plate may be attached to base 14 and member 15 in a known manner such as by welding.

On stem 12, an adjustable collar 25 with tooth rest 26 attached thereto is shown with a rubber bite ball and extension 28 attached to its opposite side. The rubber bite ball may be used in situations where tooth rest 26 is inappropriate, such as when the patient has buck teeth or lacks maxillary incisal teeth and could not make contact with tooth rest 26. The extended rubber bite ball will, however, serve the purpose of tooth rest 26 in these situations. The attachment is loosened and the bite ball rotated into position under these circumstances. A set screw 30 can be loosened to provide adjustment of collar 25.

Figure 5:
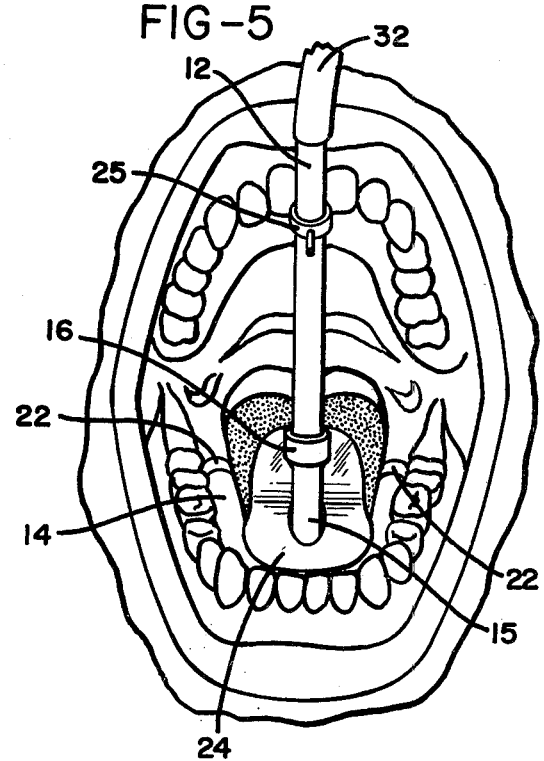
FIG. 5 is a perspective view of the suction device positioned in the open mouth of a patient.

As shown in FIG. 5, when the suction device is inserted into a patient's mouth, U-shaped base 14 is positioned in the lower jaw area inside the lower row of teeth. In this manner all excess moisture in a patient's mouth may be evacuated through slots 20 and holes 21 in base 14. The adjustable tooth rest 26 is positioned so that the patient's upper maxillary incisal teeth rest thereon and the patient's mouth is maintained in an open, but comfortable, position. Also as shown in FIG. 5, plate 24 acts as a tongue depressor and maintains the patient's tongue in a position away from the area of dental operation. The curvature of stem 12 and member 15 is such that stem 12 makes about a 45° angle with base 14.

Because of this curvature and angle of placement, the suction device is able to perform its multiplicity of functions while leaving a clear area in which the dentist can work. There is ample room to insert, position, and seat an impression tray for either crown or bridge work. Additionally, stem 12 can be disconnected quickly from member 15 at collar 16 while leaving base 14 in place. This enhances patient comfort while waiting for the impression material to set up and can be reconnected quickly without disturbing the impression if further evacuation of excess moisture in the patient's mouth is required.

While the apparatus herein described constitutes a preferred embodiment of the invention, it is to be understood that the invention is not limited to this precise apparatus, and that changes may be made without departing from the scope of the invention, which is defined in the appended claims.

What is claimed is:

1. A dental suction device comprising:
   an elongated tubular stem;
   connection means at a first end of said stem for connection with a suction line;
   a generally U-shaped, tubular base member adapted to fit in a patient's lower jaw area inside the lower row of teeth and having a short, curved, tubular member in fluid connection with said base member at about the midpoint of said base member and extending rearwardly therefrom; whereby a clear area is left for a dentist to insert, position, and seat an impression tray,
   joint at a second end of said stem for connection with said curved tubular member;
   a plurality of liquid evacuation slots in said tubular base for removing excess moisture from the mouth of a patient;
   an elliptically shaped plate spanning said short, curved, tubular member and attached thereto adapted to depress a patient's tongue when said suction device is in position in the patient's mouth; and
   an adjustable tooth rest means mounted on said stem between said first and second ends.

2. The device of claim 1 having clean-out screws attached to each end of said tubular base.

3. The device of claim 2 where said device is fabricated of stainless steel.

4. The device of claim 1 having a rubber bite ball attached to said adjustable tooth rest means.

5. The device of claim 1 wherein stem is detachable from said curved tubular member at said joint.

6. The device of claim 5 where said stem forms about a 45° angle with said base member.

7. The device of claim 1 where said elliptically shaped plate has an elliptically shaped aperture therein through which said short, curved, tubular member passes.

* * * * *